(12) United States Patent
Josephy et al.

(10) Patent No.: US 6,335,527 B1
(45) Date of Patent: Jan. 1, 2002

(54) DEVICE FOR MONITORING LATEX PROPERTIES DURING EMULSION POLYMERIZATION

(75) Inventors: Claude Josephy, Vilvoorde; Pol Breyer, Grimbergen, both of (BE)

(73) Assignee: Solvay S.A. (Société Anonyme), Brussels (BE)

( * ) Notice: Subject to any disclaimer, the term of this patent is extended or adjusted under 35 U.S.C. 154(b) by 0 days.

(21) Appl. No.: 09/229,626

(22) Filed: Jan. 13, 1999

Related U.S. Application Data (62) Division of application No. 08/711,149, filed on Sep. 10, 1996, now Pat. No. 5,898,056.

(30) Foreign Application Priority Data

Sep. 25, 1995 (BE) ............................................. 9500784

(51) Int. Cl.⁷ ............................. G01N 21/35; G01J 3/28
(52) U.S. Cl. ............................ 250/339.11; 250/339.07; 250/341.2; 250/339.09; 250/339.12
(58) Field of Search ........................... 250/338.1, 338.5, 250/339.01, 339.04, 339.07, 339.11, 341.2, 341.8; 356/319, 51

(56) References Cited

U.S. PATENT DOCUMENTS

| | | | |
|---|---|---|---|
| 4,755,048 A | | 7/1988 | Kaufman |
| 4,882,493 A | | 11/1989 | Lodder |
| 5,062,709 A | | 11/1991 | Slee |
| 5,155,184 A | | 10/1992 | Laurent |
| 5,170,056 A | * | 12/1992 | Berard et al. ................ 250/341 |
| 5,223,715 A | * | 6/1993 | Taylor ........................ 250/343 |
| 5,349,188 A | | 9/1994 | Maggard |
| 5,349,189 A | | 9/1994 | Maggard |
| 5,379,464 A | * | 1/1995 | Barnes et al. ................ 128/633 |
| 5,532,487 A | * | 7/1996 | Brearley et al. ........ 250/339.12 |
| 5,712,703 A | * | 1/1998 | Ando et al. .................. 356/319 |

FOREIGN PATENT DOCUMENTS

| | | |
|---|---|---|
| EP | 0 328 826 | 8/1989 |
| WO | 96/05498 | 2/1996 |

OTHER PUBLICATIONS

S.Y. Chang et al., "Monitoring Polymerization Reactions by Near–IR Spectroscopy." In: ACS Symposium Series: Multidimensional Spectroscopy of Polymers, vol. 598, 1995, pp. 147–165.

P.D. Gossen et al., "Composition and Particle Diameter for Styrene/Methyl Methacrylate Copolymer Latex Using UV and NIR Spectroscopy." In: Applied Spectroscopy, vol. 47, No. 11, 1993, pp. 1852–1870.

P.K. Aldridge et al., "Noninvasive Monitoring of Bulk Polymerization Using Short–Wavelength Near–Infrared Spectroscopy." In: Analytical Chemistry, vol. 47, No. 11, Dec. 1993, pp. 3581–3585.

* cited by examiner

*Primary Examiner*—Constantine Hannaher
*Assistant Examiner*—Albert Gagliardi
(74) *Attorney, Agent, or Firm*—Venable; Marina V. Schneller; Catherine M. Voorhees (57) ABSTRACT

Device for monitoring the quality of latex in a reactor during emulsion polymerization, including essentially a measuring probe placed in the reactor, an optical coupling of the said probe with a near-infrared spectrophotometer provided with means for emitting light and for capturing the scattered light which is reflected and a computer which has the correlation equations in its memory.

5 Claims, 6 Drawing Sheets

DEVICE FOR MONITORING LATEX PROPERTIES DURING EMULSION POLYMERIZATION

CROSS REFERENCE TO RELATED APPLICATION

This is a divisional application of Ser. No. 08/711,149 filed Sep. 10, 1996, now U.S. Pat. No. 5,898,056 which is relied upon and expressly incorporated by reference herein.

FIELD OF THE INVENTION

The present invention relates to a process for monitoring the quality of latices of halogen-containing vinyl polymers. It relates more particularly to a process for monitoring the quality of latices of such polymers during the radical polymerization of halogen-containing vinyl monomers in aqueous emulsion. It also relates to a device for monitoring the quality of the aqueous emulsions.

TECHNOLOGY REVIEW

Radical polymerization in aqueous emulsion, typically using, besides an aqueous polymerization medium, emulsifying agents and radical initiators, constitutes a polymerization technique which is particularly well suited to the manufacture of aqueous emulsions of halogen-containing vinyl polymers, usually called latices, such as, for example, latices of polyvinyl chloride or of vinylidene chloride copolymers. The latices thus produced contain, ultimately, elementary polymer particles which have very small mean diameters that can range from approximately 10 to approximately 4000 nm (nanometers). For some applications, such as, for example, in the field of paints or generally of coatings, these latices find an application directly without preliminary isolation of the polymers from their polymerization medium. In other applications, such as, for example, PVC-based plastisols, the polymers are isolated from their polymerization medium and dried before being used. In all cases the quality of the manufactured products is dependent in particular on the mean diameter of the polymeric elementary particles of the latex and the diameter distribution of the particles.

This is why it has been found desirable to have at one's disposal a process for effective and rapid monitoring of the quality of the latices during the polymerization in aqueous emulsion in order to have the ability of ensuring a very high reproducibility of the quality of the latices and of the polymers produced. Monitoring the progress of a polymerization, by means of measurements reflecting the properties of the polymer being formed, makes it possible, in fact, to control the polymerization conditions so as to produce polymers which have predetermined properties with an improved reproducibility.

It has already been proposed to monitor properties characterizing the molecular structure of polymers, such as the viscosity index or the density of the polymers, by means of the measurement of the absorption spectrum in the near infrared ("NIR" hereinafter) region on samples of polymers taken during polymerization and freed beforehand from their polymerization medium and, in particular, on olefin polymers in powder form (Patent Application EP-A-0 328 826). The process in question permits control of the polymerization by modifying the polymerization conditions when a predetermined difference appears between the measured properties of the isolated polymer and those which it is desired to attain. Nevertheless, the process according to document EP-A-0 328 826 requires regular sampling and analysis of samples of polymer which has been separated beforehand from its polymerization medium and is therefore not suitable for an in-situ monitoring during polymerization.

The measurement has furthermore been described (with a view to a calibration) of the spectrum transflectance in the near infrared region, ranging from 900 to 1200 nm, on the light transmitted through latices of copolymers of styrene and of methyl acrylate, with a solids content of 30% by weight, containing polymer particles whose mean diameter is approximately 60 to 80 nm (Paul D. Gossen et al., Applied Spectroscopy, vol. 47, No. 11, 1993, pp. 1852–1870). These measurements have made it possible to establish some correlations between the transflectance at specific wavelengths and some properties of the latices of copolymers of styrene and of methyl acrylate, such as the mean particle diameter and the solids content of the latices. However, this "off-line" calibration technique using the light transmitted through the latex is described as not being suitable for latices containing polymer particles whose mean diameters are from approximately 150 to 200 nm (and more). It cannot therefore be adapted to the monitoring of industrial latices whose concentration can exceed 50% at the end of polymerization, or to the determination of the mean diameters and more generally of the diameter distribution of the polymer particles in aqueous emulsions consisting of one or a number of classes of particles whose final mean diameter is generally greater than approximately 200 nm.

SUMMARY OF THE INVENTION

The present invention is aimed at providing a process for monitoring the quality of latices of halogencontaining vinyl polymers which does not exhibit any of the abovementioned disadvantages.

BRIEF DESCRIPTION OF THE DRAWINGS

The total solids content of the monitored latex, expressed in %, has been plotted as ordinate in FIG. 1. The mean diameter of the particles, expressed in micrometers ($\mu$m), has been plotted as ordinate in FIG. 2. The time, expressed in minutes, counted starting from t0, has been plotted as abscissa in FIGS. 1 and 2.

The results of the measurements are repeated in FIGS. 3 and 4, in which the abscissae also show the time, expressed in minutes, counted from t0. The total solids content of the monitored latex, expressed in %, has been plotted as ordinate in FIG. 3, and the mean particle diameter, expressed in micrometers, in FIG. 4.

DETAILED DESCRIPTION OF THE INVENTION

To this end, the invention relates to a process for monitoring the quality of latices of halogen-containing vinyl polymers during radical polymerization of halogen-containing vinyl monomers in aqueous emulsion, characterized in that a luminous radiation is emitted into the aqueous emulsion, the scattered light reflected by the polymer particles of the latex in the spectrum band situated between 1100 and 2500 nm is captured and transmitted to a near-infrared spectrophotometer, the scattered light reflected at certain specific wavelengths situated in this spectrum band, and correlated with specific properties of the latex with the aid of correlation equations stored in a memory, is measured, the measured values are introduced into the said memory and the specific property which is monitored is calculated.

The wavelengths chosen for producing the correlation between the reflected scattered light (called "reflectance" for short hereinafter) and a specific property of a polymer latex will generally be a function of the polymerization conditions, of the nature of the latex and of the halogen-containing vinyl polymer. They will be therefore have to be determined experimentally beforehand. This calibration is advantageously performed by statistical analysis on a large number of latex samples. The correlation equations are advantageously established by statistical regression. The correlation equations can then be introduced into the memory of a computer coupled to the spectrophotometer, or into the spectrophotometer itself, and the properties can be calculated directly.

As nonlimiting examples of the latex properties which may be monitored during polymerization according to the process of the invention there may be mentioned the mean particle diameter, the total solids content and therefore the degree of conversion (or degree of progress of the polymerization reaction), the diameter distribution of the particles (by classes) and therefore the detection of different classes of particles or, furthermore, the total surface area of the particles.

As examples of wavelengths which have been correlated by statistical regression with specific properties of a vinyl chloride homopolymer latex, for example, there may be mentioned:

in the case of the total solids content: 1602, 1610, 1692, 1714, 1886 and 2394 nm in the case of the mean particle diameter: 1332, 1382, 1390, 1816, 2102 and 2180 nm in the case of the class of particles of diameter from 500 to 900 nm: 1394, 1402, 1410, 2094 and 2488 nm in the case of the total surface area of the particles: 1190, 1198, 1206, 1282, 1404 and 2230 nm.

The measurement of the scattered light reflected (reflectance) at specific wavelengths is generally performed at least a certain number of times during polymerization, for example at least near the beginning of the polymerization, with a view to following the initiation, and at the end of polymerization, with a view to verifying the degree of conversion before the reactor is degassed.

In accordance with a particular embodiment of the process of the invention the monitoring of the quality of the latex of halogen-containing vinyl polymer is performed on a sample of aqueous emulsion taken during polymerization. This sampling may, for example, be performed in a bypass situated on the polymerization reactor.

In accordance with another particular embodiment, which is given preference, the process for monitoring according to the invention is performed on the aqueous emulsion directly in the polymerization reactor. In this preferred embodiment no latex sampling is needed, and the response to any departure of a property in relation to a preestablished value is even quicker. Furthermore, this embodiment has the advantage of allowing a continuous monitoring of the quality of the latices during polymerization.

A halogen-containing vinyl monomer is intended, for the purpose of the present invention, to denote any monomer which is polymerizable by a radical route, containing a terminal olefinic unsaturation and substituted by at least one halogen atom. These monomers are preferably chosen from the substituted derivatives of ethylene and of propylene and contain only two or three carbon atoms respectively. The halogen atoms are preferably chosen from chlorine and fluorine atoms. By way of nonlimiting examples of such monomers there may be mentioned vinyl chloride, vinyl bromide, vinyl fluoride, vinylidene chloride, vinylidene fluoride, chlorotrifluoroethylene, tetrafluoroethylene and hexafluoropropylene. The invention is particularly suited to the monitoring of the aqueous emulsion radical polymerization of vinyl chloride, vinylidene chloride and vinylidene fluoride.

For the purpose of the present invention polymerization is intended to denote both the homo-polymerization of halogen-containing vinyl monomers and their copolymerization with each other or with other monomers which can be copolymerized with them. Examples of the latter which may be mentioned are vinyl esters such as vinyl acetate, acrylic esters such as methyl acrylate and methyl methacrylate, unsaturated nitrites such as acrylonitrile and methacrylonitrile, allyl esters such as allyl acetate, styrene derivatives and alpha-olefins such as ethylene and propylene. However, the invention applies preferably to the monitoring of latices of polymers containing at least 50 mol % and preferably at least 80 mol % of units derived from halogen-containing vinyl monomers. It applies particularly to the monitoring of the quality of vinyl chloride polymer latices, more especially of vinyl chloride homopolymers, of vinylidene chloride copolymers and of vinylidene fluoride polymers, both homo- and copolymers.

Nonlimiting examples of vinylidene chloride polymers which may be mentioned are the copolymers containing approximately 70 to 96% by weight of vinylidene chloride, the remainder consisting essentially of alkyl acrylates such as methyl acrylate, or else of vinyl chloride.

Nonlimiting examples of vinylidene fluoride copolymers which may be mentioned are the copolymers with chlorotrifluoroethylene or with hexafluoropropylene, containing at least 75% by weight of vinylidene fluoride.

For the purpose of the present invention aqueous emulsion radical polymerization is intended to denote any radical polymerization process performed in an aqueous medium in the presence of emulsifying agents and of radical initiators. This definition specifically includes the so-called "conventional" aqueous emulsion polymerization in which water-soluble radical initiators are used, as well as the polymerization in microsuspension, also referred to as in homogenized aqueous dispersion, in which oil-soluble initiators are used and an emulsion of droplets of monomers is produced by virtue of powerful mechanical stirring and the presence of emulsifying agents.

The nature of the emulsifying agents and of the initiators, both water- and oil-soluble, is not critical. The process for monitoring according to the invention therefore applies to any aqueous emulsion process for radical polymerization of halogen-containing vinyl monomers in the presence of the initiators and of the emulsifying agents which are conventional in polymerization of this type. It is particularly suited for monitoring the "conventional" aqueous emulsion polymerization using emulsifying agents and water-soluble initiators.

The process according to the invention has the advantage of permitting the surveillance of the quality of the latices, such as, for example, the surveillance of the degree of conversion and/or of the mean size of the polymer particles, throughout the duration of the polymerization, that is to say both in the case of the low conversion ratios (beginning of the polymerization), when the latex has a low solids content and contains only particles of very small size, and in the case of high conversion ratios (end of polymerization), when the latex has a high solids content (several tens of %) and contains especially particles of large diameter.

The process according to the invention also has the appreciable advantage of allowing some properties of the latex to be measured directly during polymerization without preliminary isolation of the polymer from its polymerization medium (water in this case). As a result, it permits a very quick response in the event of departure of a latex property in relation to a preestablished value, that is to say a rapid intervention, when needed, on the parameters of the polymerization which affect the property which has "gone astray" and hence a control of the polymerization which is capable of guaranteeing a very high reproducibility of the quality of the latices produced. As nonlimiting examples of parameters which are well known to a person skilled in the art and which affect the properties of the latices of polymers during polymerization there may be mentioned polymerization temperature, the rate of stirring of the polymerization mixture, the injection programme for the reactants, such as the emulsifier and the initiator, or the introduction of one or of several other polymer latices during polymerization.

The invention also relates to a device for monitoring the quality of latices of halogen-containing vinyl polymers in a reactor during polymerization.

Figure 5:
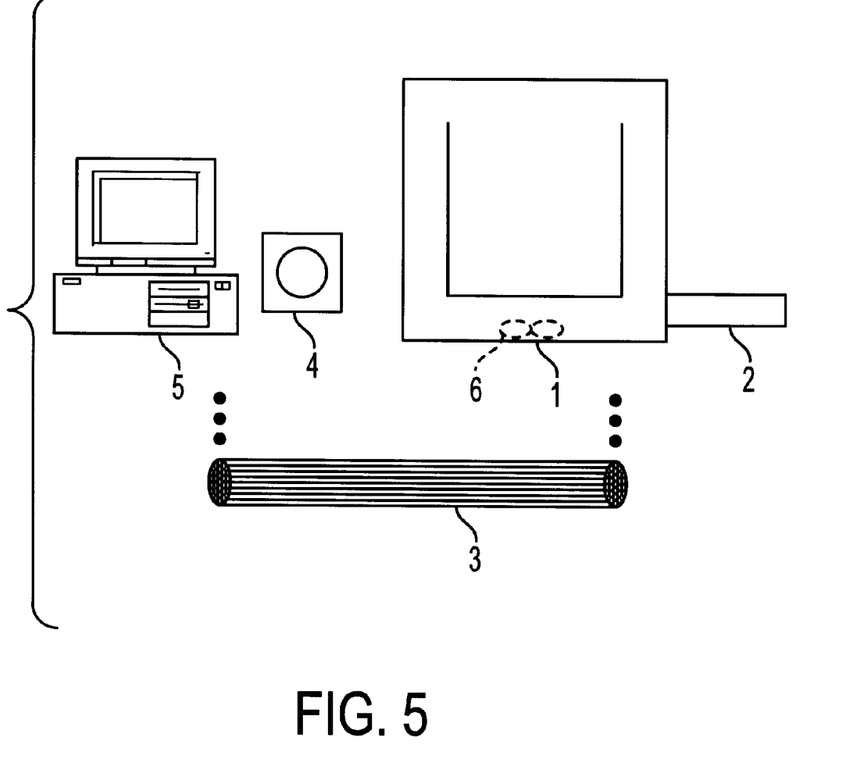
FIG. 5 is a schematic drawing of a device in accordance with the invention.

Measuring probes of this type, known as NIR probes, can be found in the trade. The optical coupling 3 between the measuring probe 2 and the near-infrared spectrophotometer 4 is advantageously produced by means of optical fibres.

It is recommended that the measuring probe 2 be placed in the bottom of the reactor 1 and, furthermore, be placed above the stirrer 6, care being taken that it is positioned in such a way that it is immersed at the beginning of polymerization (that is to say when the reactor contains the entire polymerization charge). In these conditions the monitoring measurements performed are representative of the quality of the lactices.

It is obvious that the probe placed in the reactor will need to be capable of withstanding the high pressures developed during polymerization and the partial vacua applied before polymerization with a view to removing oxygen from the reactor. It is also obvious that the probe will need to be absolutely leakproof in order to rule out any leakage of gaseous monomer.

Figure 6:
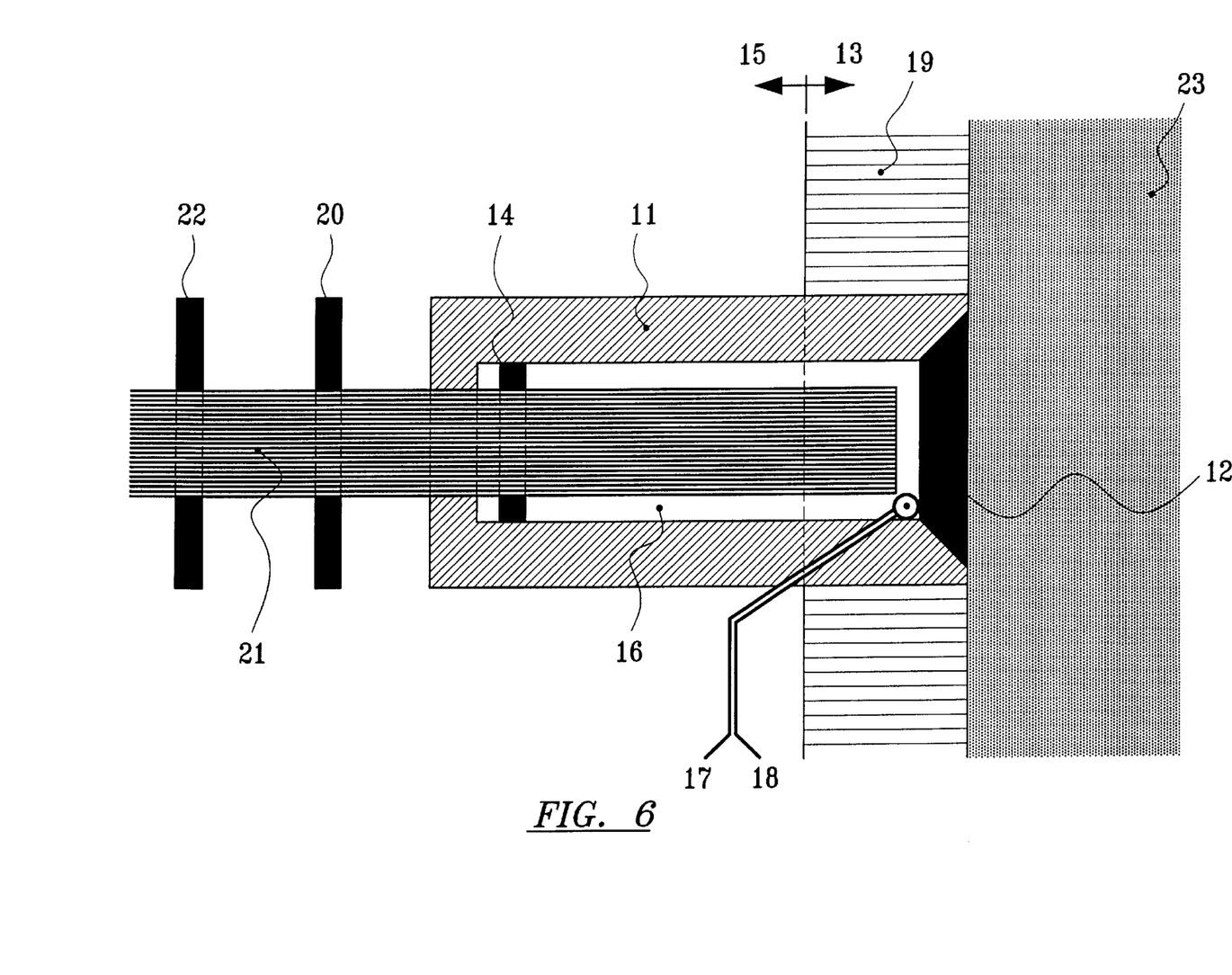
FIG. 6 is a schematic drawing of the probe according to the invention.

As shown in FIG. 6, it is recommended to employ for this purpose a probe 11 provided with two leakproof barriers: a first leakproof barrier 12 on the reactor side 13, for example a sapphire window, and a second leakproof barrier 14 on the external side 15, for example an O-ring type seal, and to maintain the interior 16 of the probe at a determined pressure of an inert gas.

The monitoring of this pressure via a pressure sensor 17 will make it possible to detect a failure of the reactor-side barrier as an increase in the pressure during the polymerization (or a drop in pressure during the evacuation stage) and a failure of the external side barrier as a drop in pressure.

In order to ensure maximum safety and to make it possible to detect a possible simultaneous failure of both leakproof barriers it is also possible to provide a detector of monomer 18, for example of vinyl chloride, at the spot where the probe enters the polymerization reactor 19. Assuming such a simultaneous failure of both leakproof barriers, an additional double protection can also be provided, namely the closure of a stopcock valve 20 which cuts the optical fibre connected to the measuring probe and ensures the leaktightness of the branch in the vessel, and the closure (after having removed the cut optical fibre) of a second stopcock valve 22 fitted in series with the first one in order to ensure an additional safety of complete leaktightness of the vessel branch.

The device according to the invention can be adapted to the monitoring of the quality of latices 23 of halogen-containing vinyl polymers in aqueous emulsion in any polymerization reactor conventionally employed for the aqueous emulsion polymerization of such monomers. These monomers are generally provided with means for introducing reactants and for discharging the polymer latex, a stirrer and a jacket for removing the heat of polymerization.

The examples which follow are intended to illustrate the process and the device according to the invention.

They relate to the homopolymerization of vinyl chloride in aqueous emulsion to produce a polyvinyl chloride latex while directly monitoring in the reactor the change in the total solids content of the polyvinyl chloride latex and in the mean diameter of the polymer particles as the polymerization progresses.

Measurements of the reflectance in the spectrum band situated between 1100 and 2500 nm at the wavelengths specifically correlated with these two properties of a vinyl chloride homopolymer latex (given above) are performed every two minutes starting from the initial filling until the end of the polymerization reaction and the degassing of residual vinyl chloride.

The invention is illustrated with reference to FIG. 5.

The examples are carried out in a laboratory reactor 1 of 6.6 liter capacity, fitted with a jacket in which a heat transfer fluid is circulating and a stainless steel conventional stirrer 6 with paddle blades. The reactor is furthermore provided with a probe 2 for measurement in the near-infrared (NIR) region, hermetically fitted through the jacket with its measuring window arranged flush with the reactor wall. This probe is situated in the bottom of the reactor below the initial filling level. The correlation equations and the calculator are incorporated in a computer 5 linked to the spectrophotometer 4 situated outside reactor 1. An optical coupler 3 is disposed between the probe 2 and the spectrophotometer 4. The optical coupler 4 is disposed between said probe and the spectrophotometer.

EXAMPLE 1

This example relates to the monitoring of the total solids content and of the mean particle diameter during the nonmicellar aqueous emulsion polymerization of vinyl chloride to produce a monomodal latex consisting of a single class of particles whose final mean diameter is approximately 300 nm. A nonmicellar aqueous emulsion polymerization is intended to denote polymerization in the presence of a quantity of emulsifier the concentration of which does not at any time exceed the critical micellar concentration of the emulsifier.

2675 g of demineralized water and 0.0075 g of copper sulphate pentahydrate (that is 7.5 cm$^3$ of a solution containing 1 g/l) are introduced in succession into the reactor at ambient temperature. The reactor is closed and the stirrer is started up at 225 rev/min. The temperature of the reactor contents is raised to 30° C. Once it has stabilized, vacuum is applied twice (to 180 mm of mercury absolute) and, between the two operations, the reactor is purged with technical nitrogen at a pressure of 600 mm of mercury absolute. 2180 g of vinyl chloride are then introduced and the temperature of the contents of the reactor is gradually raised to 51° C. The moment it reaches 51° C. 1.30 g of ammonium persulphate (that is 26 cm$^3$ of a solution containing 50 g/l) are introduced. Six minutes later 2.16 g of ammonia (that is 16 cm³ of a solution containing 135 g/l) are introduced. This moment is considered to be the zero time of the polymerization (t0).

Between t0+0 h 30 min and t0+4 h 15 min 21.8 g of myristic acid are gradually introduced (in the form of ammonium salt) (that is 242 cm³ of a solution containing 90 g/kg of myristic acid).

After a pressure drop of 2 bars the temperature is raised to 80 ° C. The stirring speed is reduced to 50 rev/min and the residual vinyl chloride is removed by degassing and stripping while boiling.

A sample of polyvinyl chloride latex is taken starting from t0+0 h 30 min and at regular intervals of approximately 30 minutes, by way of monitoring of the values obtained from the reflectance measurements. The samples taken are freed from residual vinyl chloride by degassing and stripping while boiling. The solids content (using densitometry) and the mean particle diameter, using photosedimentometry, are determined on these samples.

Figure 1:
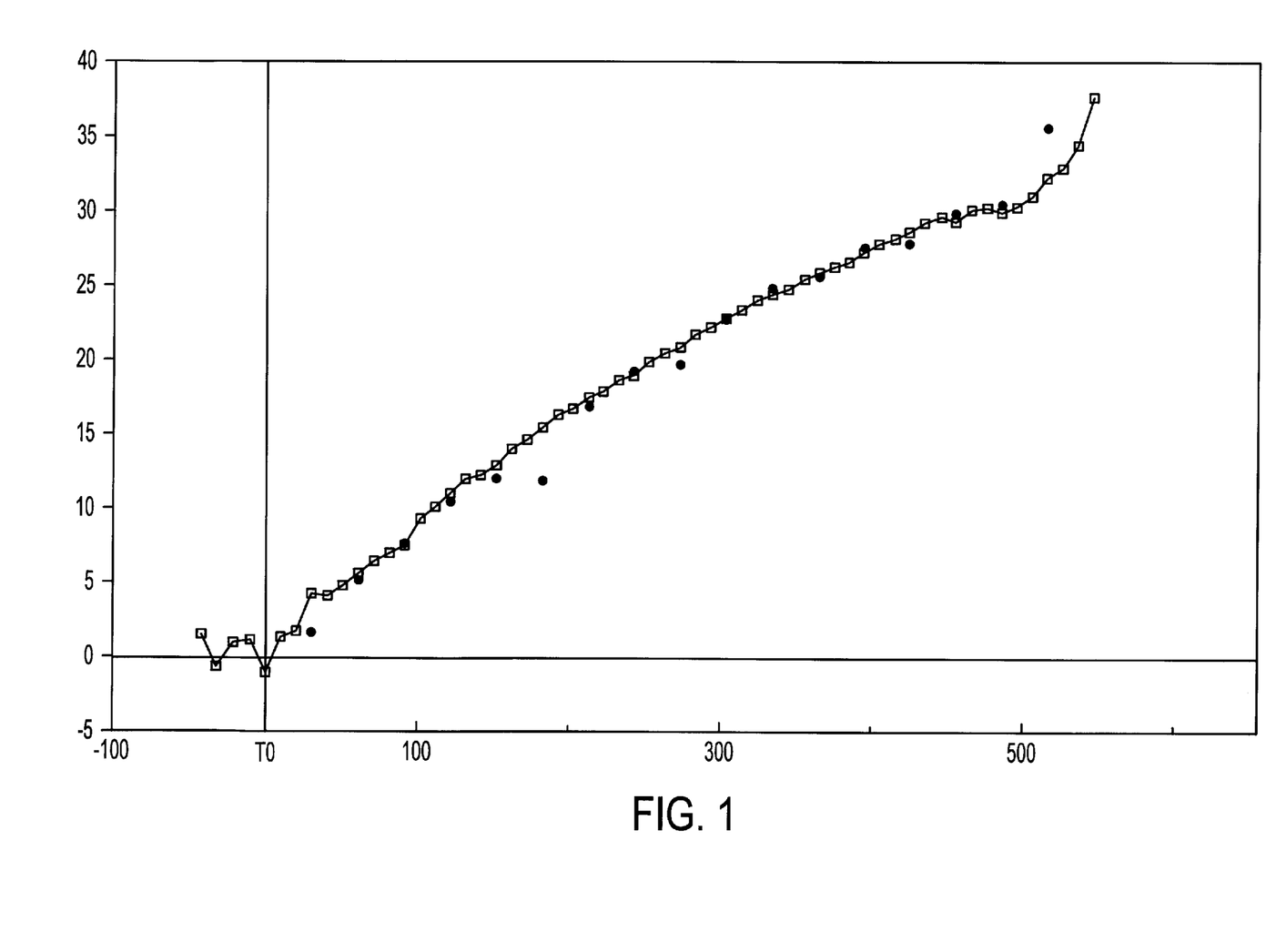

The total solids content of the monitored latex, expressed in %, has been plotted as ordinate in FIG. 1, appended. The mean diameter of the particles, expressed in micrometers ($\mu$m), has been plotted as ordinate in FIG. 2, appended. The time, expressed in minutes, counted starting from t0, has been plotted as abscissa in FIGS. 1 and 2.

Figure 2:
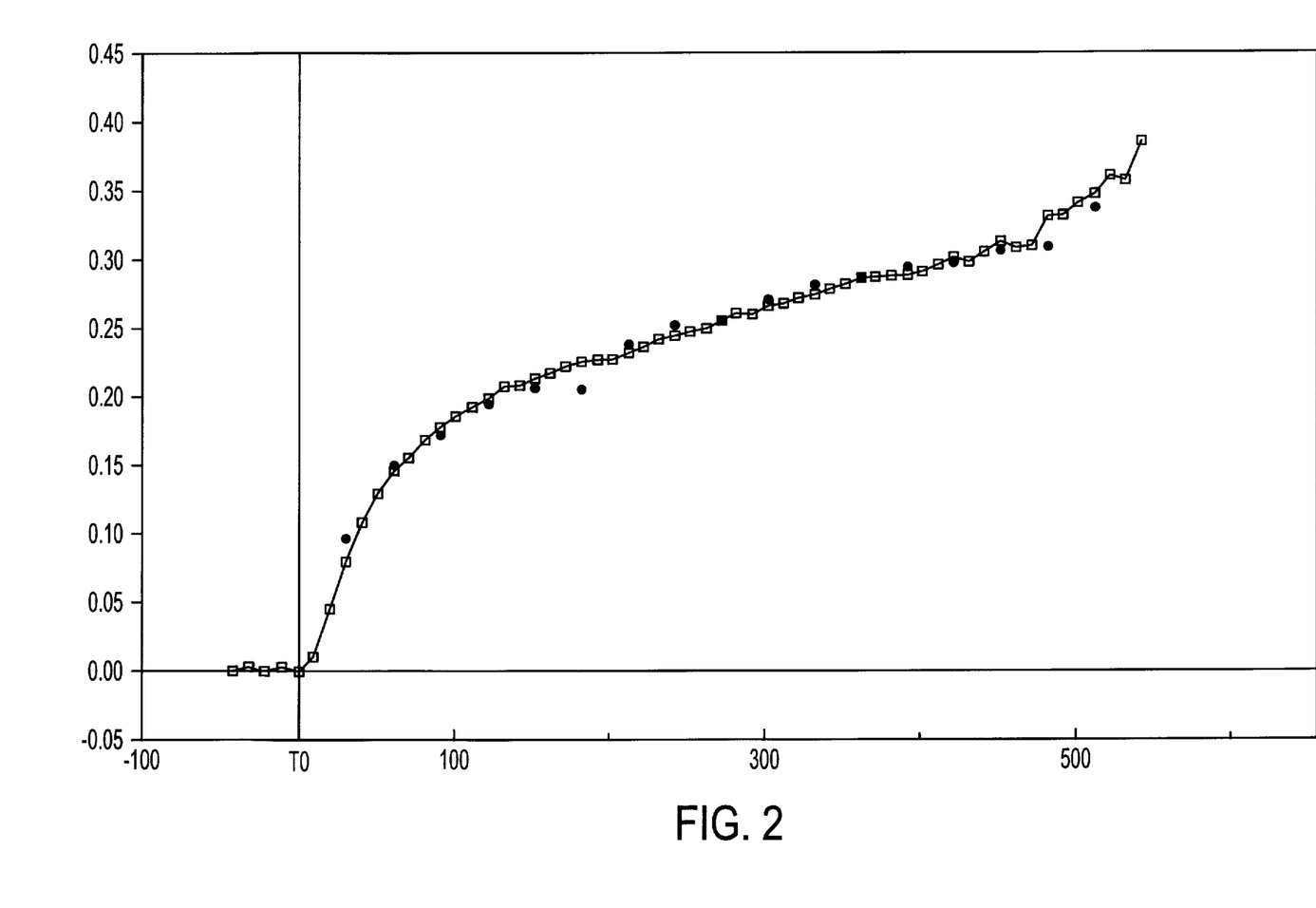

In these figures the open squares correspond to the measurements performed every two minutes according to the process of the invention and the full circles to the measurements performed every 30 minutes on samples taken during polymerization.

EXAMPLE 2

This example relates to the monitoring of the total solids content and of the mean particle diameter during the non-micellar seeded aqueous emulsion polymerization of vinyl chloride to produce a monomodal latex consisting of a single class of particles whose final mean diameter is approximately 600 nm.

2520 g of water, 0.0070 g of copper sulphate pentahydrate (that is 7 g of a solution containing 1 g/l) and 295 g of polyvinyl chloride in the form of the latex produced in Example 1 are introduced successively into the reactor. The reactor is closed and the stirrer is started up. From this moment the procedure of Example 1 is repeated in its entirety, except that the quantity (expressed in g) of the ingredients used is the following:

vinyl chloride: 1975.00 ammonium persulphate: 0.70 ammonia: 2.00 myristic acid (in salt form): 11.80

As in Example 1, the value of the reflectance at the abovementioned wavelengths is measured every two minutes via the probe directly in the aqueous emulsion and, furthermore, latex samples are taken regularly every 30 minutes and, after degassing, are analysed by way of monitoring.

Figure 3:
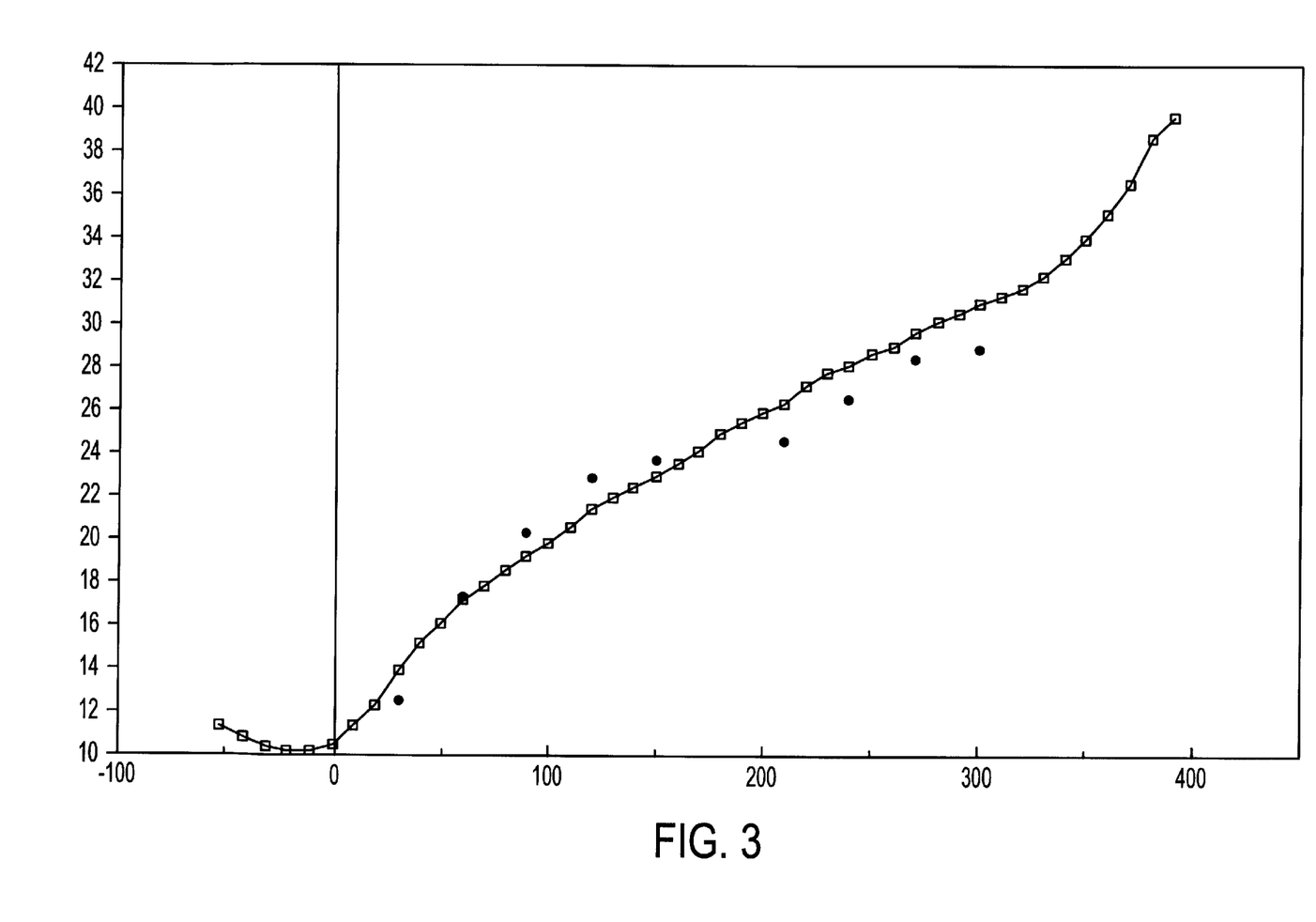
Figure 4:
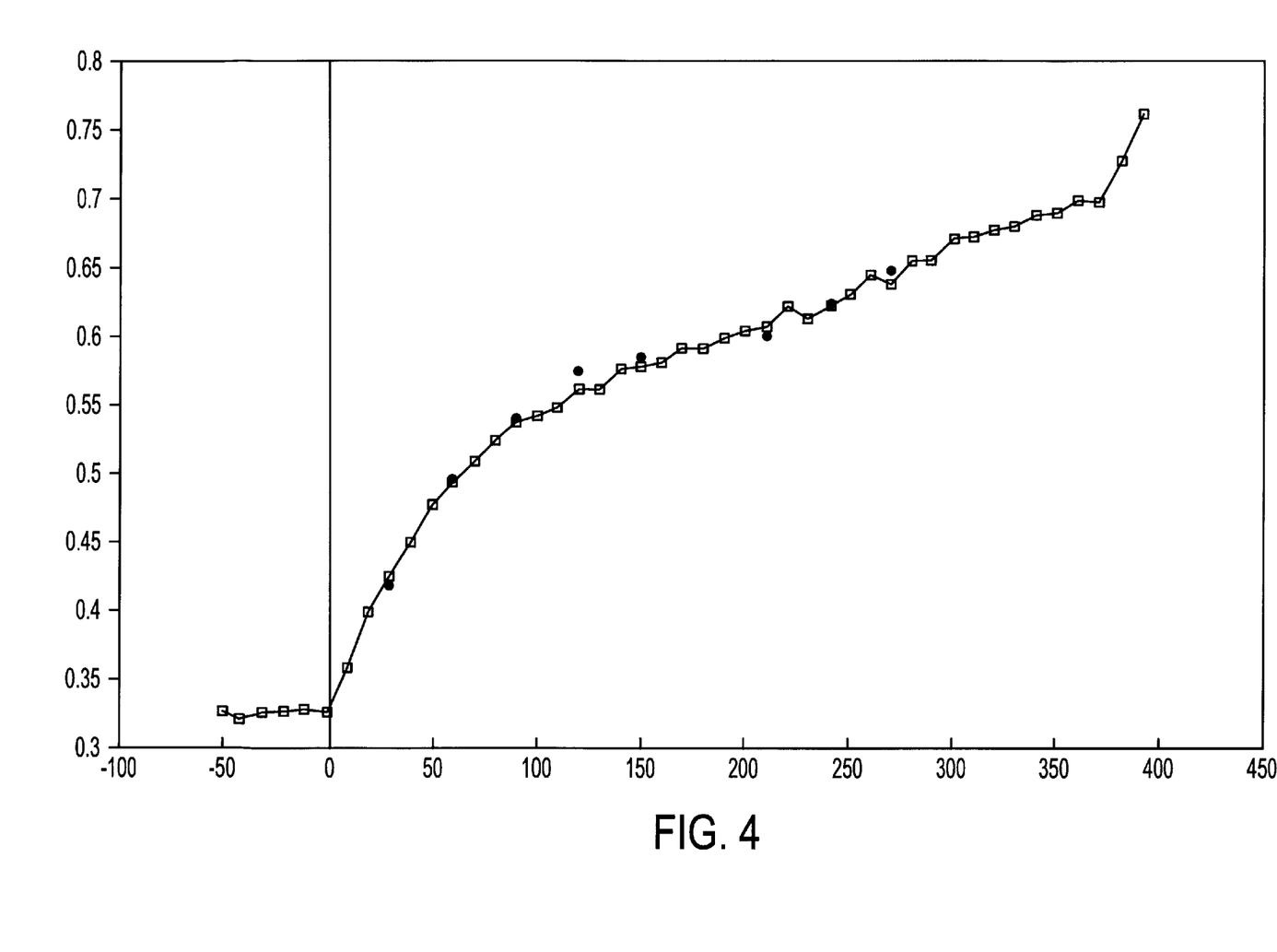

The results of the measurements are repeated in FIGS. 3 and 4, appended, in which the abscissae also show the time, expressed in minutes, counted from t0. The total solids content of the monitored latex, expressed in %, has been plotted as ordinate in FIG. 3, and the mean particle diameter, expressed in $\mu$m, in FIG. 4.

Comparison of the results shown in FIGS. 1 to 4 bears witness to the reliability and the reproducibility of the method for monitoring the quality of latices according to the invention.

What is claimed is:

1. A device for monitoring the quality of latices of halogen-containing vinyl polymers in a reactor during polymerization in aqueous emulsion, comprising:

a measuring probe placed in the reactor;

an optical coupling between said probe and a near-infrared spectrophotometer situated outside the reactor, said spectrophotometer emitting a luminous radiation and capturing the scattered light reflected in the spectrum band situated between 1100 and 2500 nm; and a computer associated with said spectrophotometer and holding in its memory equations establishing a correlation between the value of the scattered light reflected as specific wavelengths and specific properties of the latex.

2. The device according to claim 1, characterized in that the optical coupling between the measuring probe and the near-infrared spectrophotometer is produced by means of optical fibres.

3. The device in accordance with claim 1, characterized in that the probe is placed in the bottom of the reactor above the stirrer.

4. The device in accordance with claim 1, characterized in that the probe is provided with a first leakproof barrier on the reactor side and a second leakproof barrier on the external side and in that the interior of the probe is maintained at a defined pressure of an inert gas.

5. The device of claim 1, which monitors the quality of latices of halogencontaining vinyl monomers in aqueous emulsion by calculating a specific property of said latex with the aid of said equations and measured values of scattered light reflected at specific wavelengths.

* * * * *